(12) United States Patent
Wolkenstoerfer

(10) Patent No.: US 11,400,271 B2
(45) Date of Patent: Aug. 2, 2022

(54) ENTERAL FEEDING ADAPTER

(71) Applicant: N.V. NUTRICIA, Zoetermeer (NL)

(72) Inventor: Reinhold Wolkenstoerfer, Neunkirchen (DE)

(73) Assignee: N.V. Nutricia

( * ) Notice: Subject to any disclaimer, the term of this patent is extended or adjusted under 35 U.S.C. 154(b) by 501 days.

(21) Appl. No.: 16/348,395

(22) PCT Filed: Oct. 27, 2017

(86) PCT No.: PCT/EP2017/077564
§ 371 (c)(1),
(2) Date: May 8, 2019

(87) PCT Pub. No.: WO2018/086911
PCT Pub. Date: May 17, 2018

(65) Prior Publication Data
US 2019/0336743 A1    Nov. 7, 2019

(30) Foreign Application Priority Data
Nov. 10, 2016   (WO) ................. PCT/EP2016/077194

(51) Int. Cl.
*A61M 39/00* (2006.01)
*A61M 39/10* (2006.01)
(Continued)

(52) U.S. Cl.
CPC .......... *A61M 39/10* (2013.01); *A61J 15/0026* (2013.01); *A61M 39/105* (2013.01);
(Continued)

(58) Field of Classification Search
CPC ................ A61M 39/10; A61M 39/105; A61M 39/1055; A61M 2039/087;
(Continued)

(56) References Cited

U.S. PATENT DOCUMENTS 6,375,231 B1 *   4/2002  Picha ................. A61M 39/1011
                                                     285/114
10,646,705 B2 *  5/2020  Uehara ................. A61M 39/10
(Continued)

FOREIGN PATENT DOCUMENTS

CN          1694654     11/2005
CN          105813685    7/2016
(Continued)

OTHER PUBLICATIONS

Wolkenstoerfer, Reinhold, Commercial Product Specification, Purell HP548N, Lyondell Basell Industries, Jul. 7, 2015.
(Continued)

*Primary Examiner* — Nathan R Price
*Assistant Examiner* — Tania Ismail
(74) *Attorney, Agent, or Firm* — Williams Mullen; Thomas F. Bergert

(57) ABSTRACT

We generally describe an enteral feeding adapter comprising: a tube section; a crimping fixation unit arranged on said tube section at a first section of said enteral feeding adapter for releasably connecting said enteral feeding adapter with a gastrostomy tube connector; and a screw cap freely rotatably arranged around said tube section at a second section of said enteral feeding adapter for connecting said enteral feeding adapter with a screw connector.

11 Claims, 6 Drawing Sheets

(51) Int. Cl.
　　*A61J 15/00*　　　(2006.01)
　　*A61M 39/08*　　　(2006.01)

(52) U.S. Cl.
　　CPC ... *A61M 39/1055* (2013.01); *A61M 2039/087* (2013.01); *A61M 2039/1027* (2013.01); *A61M 2039/1033* (2013.01); *A61M 2039/1077* (2013.01); *A61M 2202/0482* (2013.01)

(58) Field of Classification Search
　　CPC .. A61M 2039/1027; A61M 2039/1033; A61M 2039/1077; A61M 2202/0482; A61J 15/0026; A61J 15/0015
　　See application file for complete search history.

(56) References Cited

U.S. PATENT DOCUMENTS

| | | | |
|---|---|---|---|
| 2008/0140055 A1 | 6/2008 | Shirley | |
| 2008/0183153 A1 | 7/2008 | Enns | |
| 2012/0029479 A1* | 2/2012 | Kraushaar | A61M 39/105 604/533 |
| 2013/0103003 A1* | 4/2013 | Capitaine | A61M 39/10 604/535 |
| 2016/0354594 A1 | 12/2016 | Uehara et al. | |

FOREIGN PATENT DOCUMENTS

| | | |
|---|---|---|
| EP | 3081253 | 10/2016 |
| EP | 3081254 | 10/2016 |
| WO | 2015179094 | 11/2015 |
| WO | 2016089869 | 6/2016 |
| WO | 2016171871 | 10/2016 |

OTHER PUBLICATIONS

International Standards Organization, ISO 80368-3, Small-bore connectors for liquids and gases in healthcare applications Part 3: Connectors for enteral applications, first edition Jul. 1, 2016.
Eastman Chemical Company, Eastman Tritan™ co polyester, Secondary Operations Guide, Jun. 2009.
Eastman Chemical Company, Sterilization of Medical Devices & Packaging, Sep. 2007.
Eastman Chemical Company, Copolyester MX731, Product Regulation Information Sheet, Feb. 17, 2015.
International Search Report and Written Opinion for PCT/EP2017/077564, European Patent Office, dated Jan. 26, 2018.
International Preliminary Report on Patentability for PCT/EP2017/077564, European Patent Office, dated Mar. 22, 2019.
European Examination Report, European Patent Office for EP Application No. 17 791 088.2, dated Jun. 28, 2021.
Chinese Patent Office, Office Action for CN Application 201780069832.0, dated Feb. 1, 2021.

* cited by examiner

ENTERAL FEEDING ADAPTER

CROSS-REFERENCE TO RELATED APPLICATIONS

This application is the U.S. national phase of international application PCT/EP2017/0772564, filed on Oct. 27, 2017, which claims the benefit of international application PCT/EP2016/077194 filed on Nov. 10, 2016; all of which are hereby incorporated herein in their entirety by reference.

FIELD OF THE INVENTION

This invention generally relates to an enteral feeding adapter and a gastrostomy tube connector assembly in which the enteral feeding adapter is connected to a gastrostomy tube Y-connector.

BACKGROUND TO THE INVENTION

The ISO ("International Organization for Standardization") 80369 was developed in order to specify certain requirements when administering medication into a patient's alimentary canal. Furthermore, the ISO 80369 generally aims at addressing incidents in which enteral solutions have been administered via incorrect routes, including intravenously and into the airway.

As a result, the International Organization for Standardization identified the need to develop specific connectors and adapters for medical devices and their accessories which are used to deliver feed via the enteral route.

In ISO 80369-3, which relates to "Small-bore connectors for liquids and gases in healthcare applications—Part 3: Connectors for enteral application" (ISO Reference number ISO 80369-3:2016(E); First edition, published on 1 Jul. 2016), the design, dimensions and drawings of small-bore connectors used in enteral applications are outlined.

FIG. 1 shows an example male E1 small-bore connector taken from ISO 80369-3. According to the standardization, such a male E1 small-bore connector must comply with certain size requirements. For example, the length of the taper, the outside diameter of the larger end of the male taper at e (see FIG. 1) from the tip of the male taper, the length of the nozzle, the diameter of the smallest cylinder that encompasses the outside surfaces of external features at the open end of the collar, and other dimensions must comply with the standardization requirements.

Prior art regarding a male connector which may be provided at an upstream end of a tube used in enteral feeding can be found, for example, in EP 3 081 253 A1. In some example implementations described therein, a luer portion constitutes the male connector, whereby a lock portion is arranged so as to oppose the luer portion. A male luer may be inserted into the lock portion from the lower side thereof. The lock portion may be rotated relative to the luer portion, thus screwing a spiral protrusion and a female threading together. As the lock portion is rotated, the male luer and a tubular portion may advance inside the lock portion. A pair of protruding portions of the lock portion may then come into contact with the upper face of a flange of the luer portion, and slide thereon. The pair of protruding portions are hereby fitted into a pair of receding portions of the luer portion, and, at the same time, the lower face of the lock portion and the upper face of the flange come into contact or approach each other. When the pair of protruding portions are fitted into the pair of receding portions, the rotation torque for rotating the lock portion changes, and the operator can feel that change as a clicking sensation through their fingers. In order to remove the male connector from the tube to which the male connector is attached, the protruding portions and the receding portions hereby need to be disengaged, and a large amount of rotation torque needs to be applied for disengagement.

A problem has arisen though as users of enteral appliances, in which the above-identified connectors are used, have not been able to disconnect a female connector at the feeding set with a male connector at the gastrostomy tube due to the cold welding effect. As a result, users may pull out the complete male connector/adapter out of, for example, a gastrostomy tube Y-connector, because the fixation of the male connector/adapter to the gastrostomy tube Y-connector is not strong enough.

There is therefore a need for further improvements of enteral connectors/adapters while still complying with the ISO 80369.

SUMMARY OF THE INVENTION

According to an aspect of the present invention, there is therefore provided an enteral feeding adapter comprising: a tube section; a crimping fixation unit arranged on the tube section at a first section of the enteral feeding adapter for releasably connecting the enteral feeding adapter with a gastrostomy tube connector; and a screw cap freely rotatably arranged around the tube section at a second section of the enteral feeding adapter for connecting the enteral feeding adapter with a screw connector.

The inventors have realized that by providing an enteral feeding adapter with a rotatable screw cap, in particular a screw cap freely rotatably arranged around the tube section, and a crimping fixation unit, connecting the adapter to a gastrostomy tube connector, such as a gastrostomy tube Y-connector, on one side and to, for example, a female screw connector on the other side (or another side, which may not necessarily be the opposite side if the enteral feeding adapter is to provide for an angled connection between, for example, a gastrostomy tube Y-connector and a female screw connector), connecting and disconnecting the different parts of the system may be simplified.

The cone of the enteral feeding adapter tube section and the cone of a connector to which the adapter may be connected provide for a contact on whose surface a lipid may accumulate. By providing an enteral feeding adapter according to embodiments described herein, the enteral feeding adapter may be easily disconnected from, for example, a female screw connector as the screw cap of the enteral feeding adapter is freely rotatable around the tube section. This provides for a significant advantage over adapters in which the screw cap is in direct contact with the cone of the adapter and over adapters in which mating protruding portions and receding portions are provided on certain parts of the adapter such that rotating the screw cap requires a larger torque compared to that needed to rotate the screw cap of embodiments described herein.

It is to be noted that any references throughout the present disclosure as to the screw cap being freely rotatably arranged around the tube section may, according to some example implementations, be understood as to no additional protruding portions or parts (and/or mating receding portions or parts) being comprised in or coupled to the adapter or certain features thereof. Therefore, any torque which may be required in order to rotate the screw cap around the tube section may be kept to a minimum. Hence in some example implementations, the screw cap being freely rotatably arranged around the tube section may be understood as to a torque needed to rotate the screw cap around the tube section (in an engaged state between the screw cap and the tube section) being no larger than a predetermined torque which is just large enough to overcome a friction between the surface of the screw cap and the surface of the tube section (but not larger than that), by which surfaces the screw cap and the tube section contact each other (without, for example, any further protruding or receding features being provided on the screw cap and/or the tube section which may, as will be appreciated, influence the torque needed to rotate the screw cap around the tube section). As will be understood, the predetermined torque may hereby be given, for example, based on the materials used for the screw cap and the tube section.

We note that the cone of the enteral feeding adapter tube section of embodiments described herein may be disconnected from the cone of, for example, a female screw connector to which the enteral feeding adapter is connected.

In a preferred embodiment of the enteral feeding adapter, the crimping fixation unit comprises a crimp ring. This may be particularly advantageous as a continuous contact between the crimping fixation unit and the gastrostomy tube connector (for example a gastrostomy tube Y-connector) around the entire circumference of an inner wall of the crimping fixation unit which contacts the gastrostomy tube connector may provide for a stronger connection between the enteral feeding adapter and the gastrostomy tube connector.

In a further preferred embodiment of the enteral feeding adapter, the crimping fixation unit comprises a clamp structure for gripping a first end portion of a said gastrostomy tube connector, wherein the first end portion has a larger diameter than a second portion of the gastrostomy tube connector adjacent the first end portion. By providing a clamp (or more clamps), the connection between the enteral feeding adapter and the gastrostomy tube connector may be further strengthened.

It will be understood that in embodiments of the enteral feeding adapter in which the crimping fixation unit comprises a crimp ring, the clamp structure may provide for a form closure in which a diameter of the crimp ring at a first section, which is in contact with, for example, a gastrostomy tube Y-connector first when the enteral feeding adapter and the gastrostomy tube Y-connector are connected, may be smaller than the diameter of the crimp ring at a second section which is closer to the center of the enteral feeding adapter than the first section. Such a structure may provide for a gripping effect, whereby the gastrostomy tube Y-connector may snap-fit into the crimp ring.

In a further preferred embodiment of the enteral feeding adapter, the crimping fixation unit comprises one or more protrusions on an inner surface of the crimping fixation unit, wherein the one or more protrusions are configured to increase a friction coefficient between an outer wall of a said gastrostomy tube connector (for example a gastrostomy tube Y-connector) and the inner wall of the crimping fixation unit when the gastrostomy tube connector is inserted into the crimping fixation unit. In some embodiments, the one or more protrusions may thereby cut (at least partially) into the gastrostomy tube connector when the gastrostomy tube connector is inserted into the crimping fixation unit. The skilled person will appreciate that in embodiments, in which one or more protrusions are used, a different material may be used for the enteral feeding adapter (or at least the crimping fixation unit, or in fact at least the one or more protrusions) compared to that of the gastrostomy tube connector to which the enteral feeding adapter is connected, in order to allow the one or more protrusions to cut into the material of the gastrostomy tube connector.

In a further preferred embodiment of the enteral feeding adapter, the crimping fixation unit comprises a volume which tapers in a direction along which a said gastrostomy tube connector is to be inserted into the volume. A force above a threshold may thereby need to be applied in order to guide the gastrostomy tube connector into the crimping fixation unit. However, once the gastrostomy tube connector may hit a stopper of the crimping fixation unit (or the enteral feeding adapter) or an end portion of the crimping fixation unit, the connection between the gastrostomy tube connector and the enteral feeding adapter may be strengthened even further due to the tapered shape of the above-specified volume.

In a further preferred embodiment of the enteral feeding adapter, the crimping fixation unit and/or said tube section comprises copolyester. It may be important that the enteral feeding adapter through which enteral feed may be transported is particularly resistant to lipids. It may therefore be advantageous to provide a crimping fixation unit and/or tube section comprising copolyester which is particularly resistant to lipids. The inventors have further found that making mating parts out of copolyester allows for an easy disconnection of the mating parts when desired. In a further preferred embodiment of the enteral feeding adapter, the copolyester comprises Tritan™ Copolyester MX 731 (see, for example, http://ws.eastman.com/ProductCatalogApps/PageControllers/ProdDatasheet_PC.aspx?Product=71070461&sCategoryName=Generic) as it allows increasing the clamping persistency even further.

In a further preferred embodiment of the enteral feeding adapter, the screw cap comprises polypropylene. As will be described below, the screw cap may be snap-fit onto the tube section by slipping legs or a section of the screw cap with a smaller diameter than the other sections (or at least a neighboring section) of the screw cap over protrusions which may be provided on the tube section. Polypropylene exhibits properties which allow for the screw cap to be easily slipped over the protrusions of the tube section. Furthermore, polypropylene has a relatively high elasticity compared to other (plastic) materials which are generally used for enteral feeding adapters, such that breaking of parts of the screw cap and/or the tube section may be prevented during the mounting process. In a further preferred embodiment of the enteral feeding adapter, the polypropylene comprises Purell HP548N (see, for example, https://www.lyondellbasell.com/globalassets/documents/polymers-technical-literature/purell-hp548n-product-information-.pdf), which exhibits particularly advantageous elasticity and gliding properties allowing for easily connecting or dis-connecting the screw cap and the tube section.

In a further preferred embodiment of the enteral feeding adapter, the tube section and the crimping fixation unit are integral to a single unit. This may allow for a simplified manufacturing of the tube section/crimping fixation unit of the enteral feeding adapter by, for example, molding the single unit.

In a related aspect of the present invention, there is provided a gastrostomy tube connector assembly comprising the enteral feeding adapter as described herein with regard to any one or more embodiments; and a gastrostomy tube Y-connector connected to the enteral feeding adapter via the crimping fixation unit.

In a preferred embodiment of the gastrostomy tube connector assembly, a first end portion of the gastrostomy tube Y-connector at which the gastrostomy tube Y-connector is connected to the crimping fixation unit has a larger diameter than a second portion of the gastrostomy tube Y-connector adjacent the first end portion. This may be particularly advantageous as, for example, a corresponding clamp structure provided on the crimping fixation unit may thereby interact with the gastrostomy tube Y-connector and secure the latter safely due to a snap-fit of the gastrostomy tube Y-connector in a corresponding form closure of the crimping fixation unit.

Further to the above, and with regard to a related aspect according to the present disclosure, we describe an enteral feeding adapter comprising: a tube section; a crimping fixation unit arranged on the tube section at a first section of the enteral feeding adapter for releasably connecting the enteral feeding adapter with a gastrostomy tube connector; and a screw cap rotatably arranged around the tube section at a second section of the enteral feeding adapter for connecting the enteral feeding adapter with a screw connector.

Preferred embodiments, variants and implementations of the above-specified enteral feeding adapter according to the aspect of the present invention and the gastrostomy tube connector assembly may equally be applied to and/or used with respect to the enteral feeding adapter regarding the above-outlined related aspect according to the present disclosure.

BRIEF DESCRIPTION OF THE DRAWINGS

These and other aspects of the invention will now be further described, by way of example only, with reference to the accompanying figures, wherein like reference numerals refer to like parts, and in which.

DETAILED DESCRIPTION OF PREFERRED EMBODIMENTS

Figure 1:
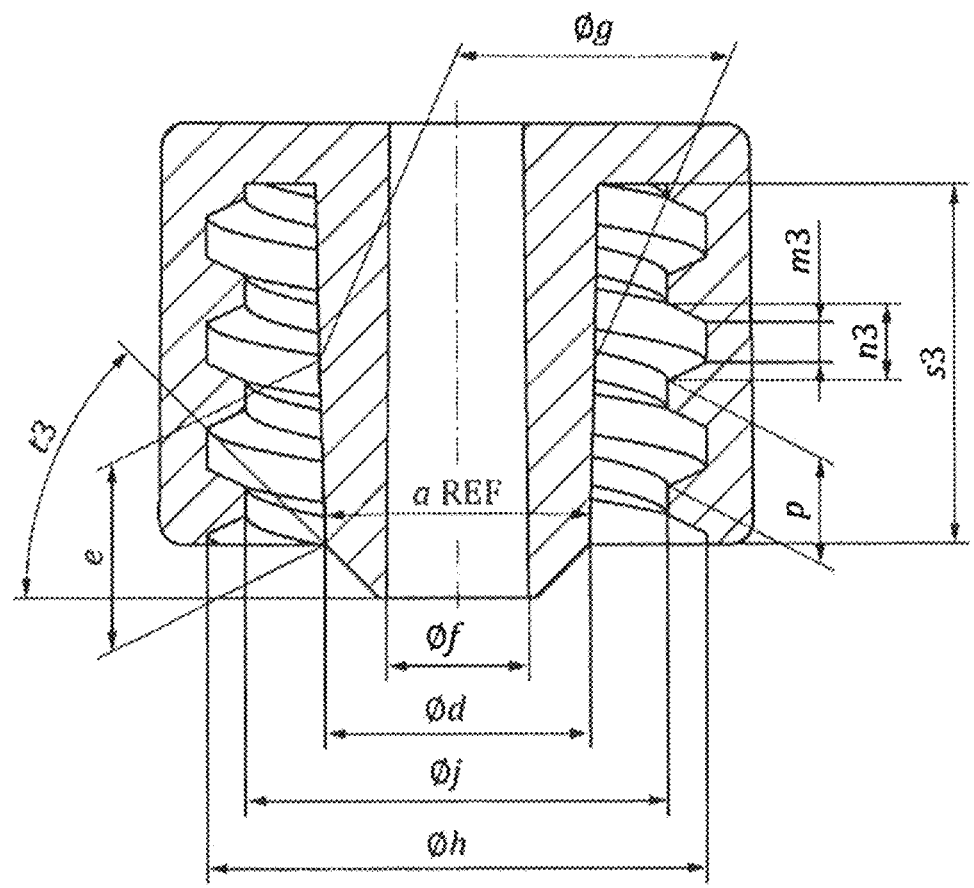
FIG. 1 shows a schematic cross-sectional side view of a male small-bore connector of the prior art.
Figure 2:
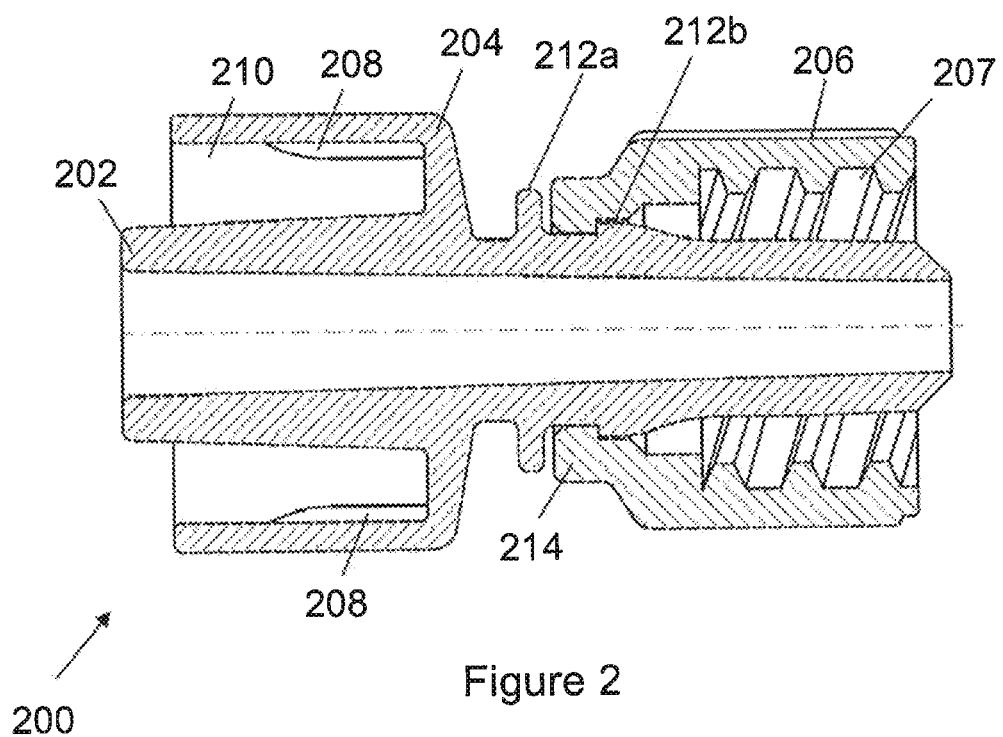
FIG. 2 shows a schematic cross-sectional side view of an enteral feeding adapter according to embodiments of the present invention.

FIG. 2 shows a schematic cross-sectional side view of an example of an enteral feeding adapter 200 as described herein.

The tube section 202 of the enteral feeding adapter 200 tapers from one side to the other side according to the standardization requirements. In this example, the diameter of the inner wall of the tube section 202 tapers from 4 mm to 2.9 mm. The total length of the tube section 202 is, in this example, 28.3 mm.

The enteral feeding adapter 200 has, in this example, a crimp ring 204 with an inner diameter which tapers towards the center of the enteral feeding adapter 200 in order to increase a friction coefficient between the crimp ring 204 and, for example, a gastrostomy tube Y-connector which may be inserted into the volume 210. The width of the crimp ring 204 along the longitudinal direction of the enteral feeding adapter 200 is approximately 6.5 mm.

The enteral feeding adapter 200 further comprises a screw cap 206 having a screw thread 207 via which a further screw connector, for example a female screw connector, may be connected to the enteral feeding adapter 200.

The crimp ring 204 comprises, in this example, six protrusions 208 with a length along a direction parallel to the tube section 202 of approximately 5.2 mm. As outlined above, these protrusions 208 may then increase the above-stated friction coefficient even further as the protrusions 208 may cut into the material of the gastrostomy tube Y-connector when the Y-connector is inserted into the volume 210 of the crimp ring 204.

The enteral feeding adapter 200 further comprises, in this example, protrusions 212a and 212b. Protrusion 212a (which is, in this example, a ring protrusion provided around the entire circumference of the enteral feeding adapter 200, but may also comprise one or more individual protrusions) is used in this example as a stopper preventing the screw cap 206 from sliding too far towards the side of the enteral feeding adapter 200 at which the crimp ring 204 is arranged. Protrusion 212b (which is, in this example, a ring protrusion provided around the entire circumference of the enteral feeding adapter 200, but may also comprise one or more individual protrusions) is used in this example in order to prevent the screw cap 206 from falling off the tube section 202 once the screw cap 206 is snap-fit onto the tube section 202. The screw cap 206 is hereby provided with a clamp structure 214 (which is in this example a circular part of the screw cap 206 having a smaller diameter than a neighboring section of the screw cap 206) which allows the screw cap 206 to be snap-fit onto the tube section 202.

Figure 3:
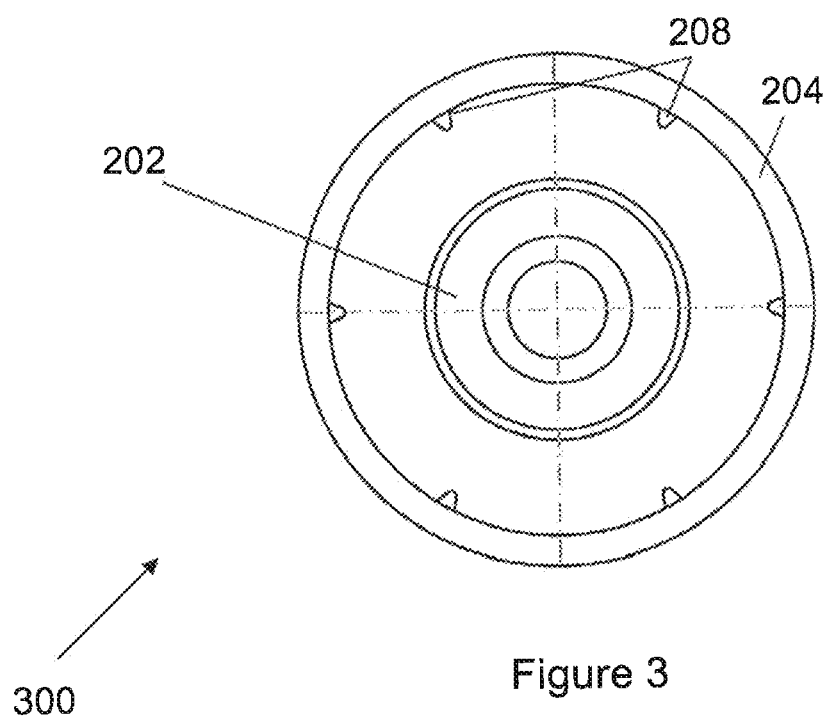
FIG. 3 shows a schematic cross-sectional view of a crimping fixation unit according to embodiments of the present invention.

FIG. 3 shows a schematic cross-sectional view of an example of a crimping fixation unit 300 as described herein. In this example, the crimping fixation unit comprises a crimp ring 204 and protrusions 208 mounted on the inner wall of the crimp ring 204.

In this example, six protrusions 208 are mounted on the inner wall of the crimp ring 204, each protrusion 208 having a width of 0.59 mm in a direction perpendicular to the direction of the tube section 202. The diameter of the crimp ring 204 is in this example 15.7 mm.

Figure 4:
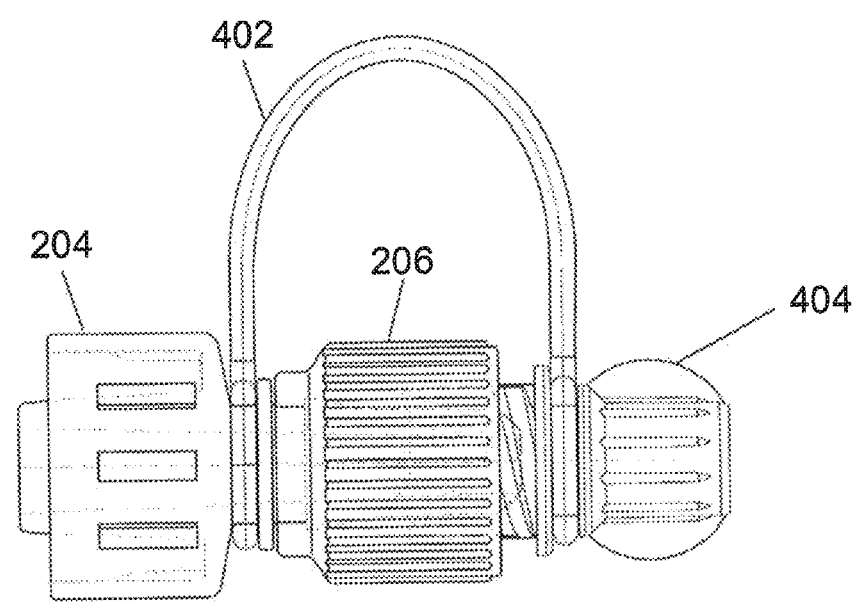
FIG. 4 shows a schematic side view of an enteral feeding adapter according to embodiments of the present invention.

FIG. 4 shows a schematic side view of an example of an enteral feeding adapter 400 as described herein.

The enteral feeding adapter 400 comprises a screw plug 404 connected to the enteral feeding adapter 400 via a strap 402. The screw plug 404 may be inserted into the screw cap 206 when the enteral feeding adapter 400 is not connected to a (e.g. female) screw connector. The strap 402 allows preventing the screw plug 404 from being lost when the screw plug 404 is not inserted into the screw cap 206.

Figure 5:
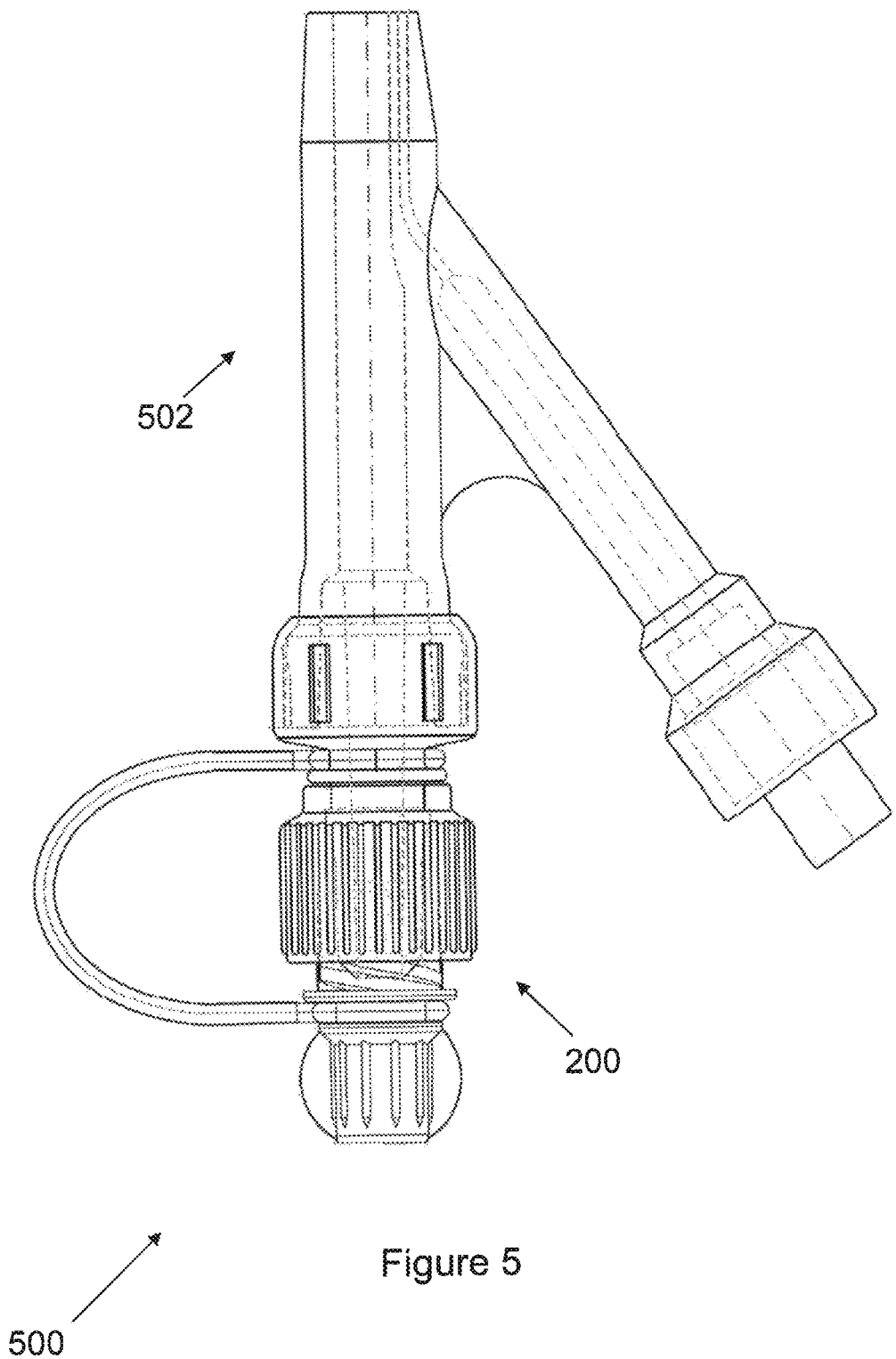
FIG. 5 shows a schematic side view of a gastrostomy tube connector assembly according to embodiments of the present invention.

FIG. 5 shows a schematic side view of an example of a gastrostomy tube connector assembly 500 as described herein. In this example, the enteral feeding adapter 200 is connected to a gastrostomy tube Y-connector 502.

In this example, the length of the gastrostomy tube Y-connector 502 is approximately 47 mm and the length of the entire gastrostomy tube connector assembly 500 is approximately 75 mm.

As can be seen from FIG. 5, the diameter of the gastrostomy tube Y-connector 502 at the end at which it is connected to the enteral feeding adapter 200 is larger compared to other sections of the gastrostomy tube Y-connector 502, thereby allowing a snap-fit of the enteral feeding adapter 200 onto the gastrostomy tube Y-connector 502 via their mating features. A particularly strong connection between the enteral feeding adapter 200 and the gastrostomy tube Y-connector 502 is thereby established.

Figure 6A:
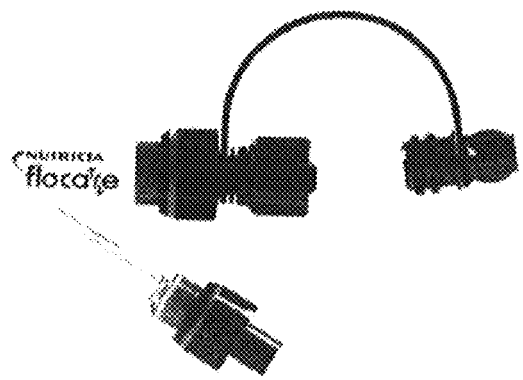
FIGS. 6a-c show side views of a gastrostomy tube connector assembly according to embodiments of the present invention.
Figure 6B:
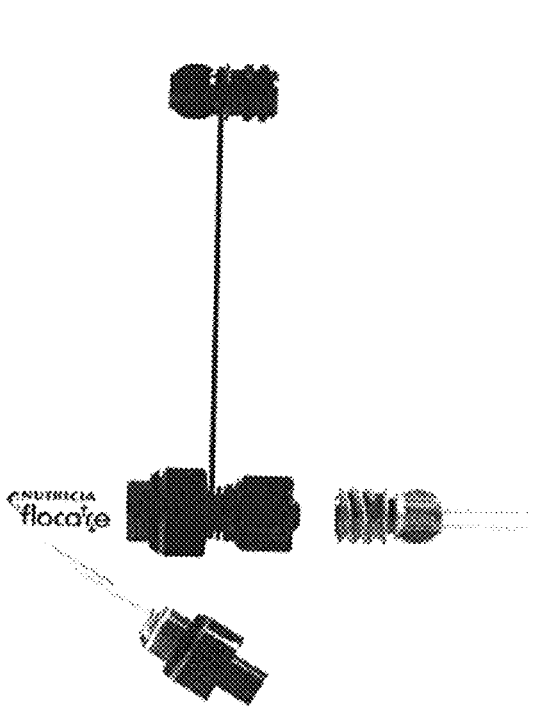
Figure 6C:
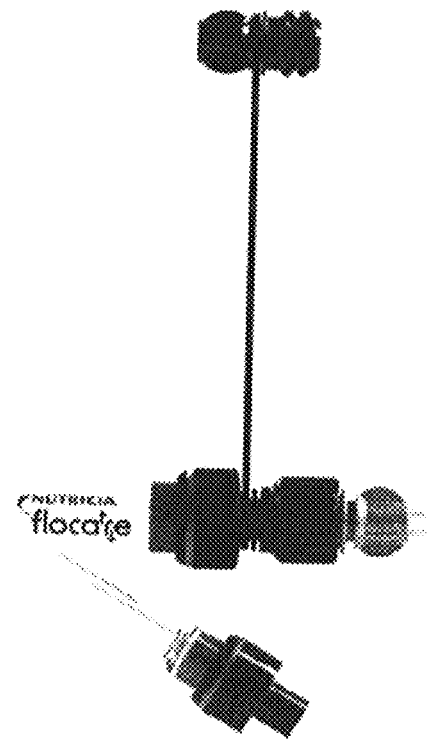

FIGS. 6a-c show side views of the gastrostomy tube connector assembly of FIG. 5 in use. As shown in FIG. 6a, the screw plug is removed from the screw cap. Due to the strap, the screw plug may not need to be stowed elsewhere while not being used. A screw connector is then inserted into the screw cap of the enteral feeding adapter. The screw connector is hereby connected and secured to the enteral feeding adapter by rotating the screw cap around the tube section of the enteral feeding adapter while the screw connector is pushed into the screw cap.

Figure 7:
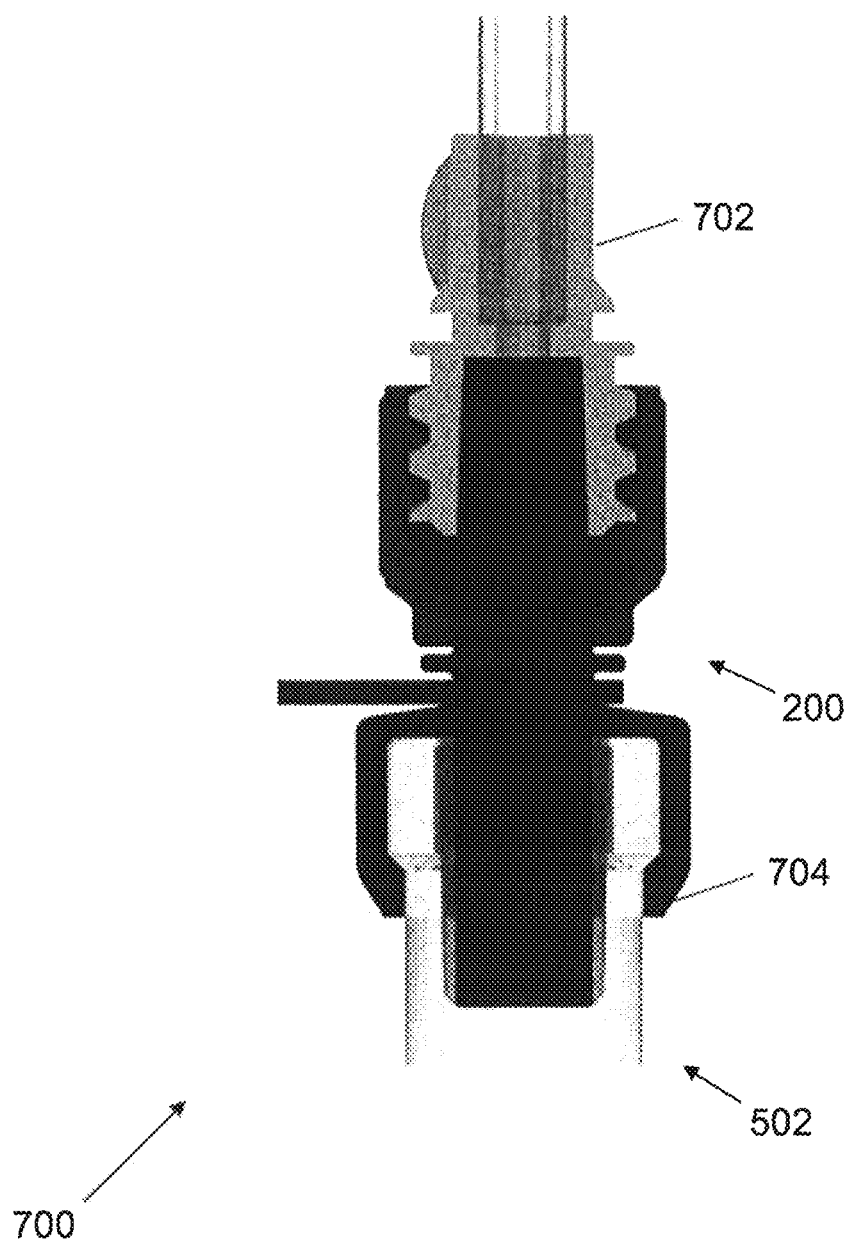
FIG. 7 shows a schematic cross-sectional side view of an enteral feeding adapter according to embodiments of the present invention in use.

FIG. 7 shows a schematic side view of an example of a gastrostomy tube connector assembly 700 as described herein.

In this schematic representation, a screw connector 702 is inserted into the screw cap of the enteral feeding adapter 200. Furthermore, the enteral feeding adapter 200 is connected to a gastrostomy tube connector 502 via the crimp ring.

In this example, the crimp ring comprises a clamp structure 704 which allows for a snap-fit of the gastrostomy tube connector 502 into the crimp ring. It is to be noted that parts of the clamp structure 704 are omitted in FIG. 7 merely to improve visualization of the gastrostomy tube connector assembly.

No doubt many other effective alternatives will occur to the skilled person. It will be understood that the invention is not limited to the described embodiments and encompasses modifications apparent to those skilled in the art and lying within the spirit and scope of the claims appended hereto.

The invention claimed is:

1. An enteral feeding adapter comprising:
   a tube section;
   a crimping fixation unit arranged on said tube section at a first section of said enteral feeding adapter for releasably connecting said enteral feeding adapter with a gastrostomy tube connector, wherein said crimping fixation unit comprises a volume which tapers in a direction along which said gastrostomy tube connector is to be inserted into said volume, wherein said volume surrounds an external surface of said tube section, wherein said tube section and said crimping fixation unit are integral to a single unit; and
   a screw cap freely rotatably arranged around said tube section at a second section of said enteral feeding adapter for connecting said enteral feeding adapter with a screw connector.

2. An enteral feeding adapter as claimed in claim 1, wherein said crimping fixation unit comprises a crimp ring.

3. An enteral feeding adapter as claimed in claim 1, wherein said crimping fixation unit comprises a clamp structure for gripping a first end portion of said gastrostomy tube connector, wherein said first end portion has a larger diameter than a second portion of said gastrostomy tube connector adjacent said first end portion.

4. An enteral feeding adapter as claimed in claim 1, wherein said crimping fixation unit comprises one or more protrusions on an inner surface of said crimping fixation unit, wherein said one or more protrusions are configured to increase a friction coefficient between an outer wall of said gastrostomy tube connector and said inner wall of said crimping fixation unit when said gastrostomy tube connector is inserted into said crimping fixation unit.

5. An enteral feeding adapter as claimed in claim 1, wherein said screw cap being freely rotatably arranged around said tube section comprises a torque needed to rotate said screw cap around said tube section, in an engaged state between said screw cap and said tube section, being no larger than a predetermined torque which is only large enough to overcome a friction between a screw cap surface and a tube section surface by which surfaces said screw cap and said tube section contact each other.

6. An enteral feeding adapter as claimed in claim 1, wherein said crimping fixation unit and/or said tube section comprises copolyester.

7. An enteral feeding adapter as claimed in claim 6, wherein said copolyester comprises
   a polymer of dimethyl terephthalate, 1,4-cyclohexanedimethanol, and 2,2,4,4-tetramethylcyclobutane-1,3-diol (TMCD), and
   an additive.

8. An enteral feeding adapter as claimed in claim 1, wherein said screw cap comprises polypropylene.

9. An enteral feeding adapter as claimed in claim 8, wherein said polypropylene comprises a homopolymer for injection moulding with nucleation and antistatic additivation.

10. A gastrostomy tube connector assembly comprising:
    the enteral feeding adapter of claim 1; and
    a gastrostomy tube Y-connector connected to said enteral feeding adapter via said crimping fixation unit.

11. A gastrostomy tube connector assembly as claimed in claim 10, wherein a first end portion of said gastrostomy tube Y-connector at which said gastrostomy tube Y-connector is connected to said crimping fixation unit has a larger diameter than a second portion of said gastrostomy tube Y-connector adjacent said first end portion.

* * * * *